United States Patent
Anderson

(10) Patent No.: US 7,041,782 B2
(45) Date of Patent: May 9, 2006

(54) LECTIN SS3939 DNA AND POLYPEPTIDES

(75) Inventor: Dirk M. Anderson, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 568 days.

(21) Appl. No.: 09/887,855

(22) Filed: Jun. 22, 2001

(65) Prior Publication Data

US 2002/0058310 A1     May 16, 2002

Related U.S. Application Data

(63) Continuation of application No. PCT/US99/30523, filed on Dec. 22, 1999.

(60) Provisional application No. 60/113,820, filed on Dec. 23, 1998.

(51) Int. Cl.
  C07K 1/00   (2006.01)
  G01N 33/53  (2006.01)
  C12P 21/06  (2006.01)

(52) U.S. Cl. ............ 530/295; 530/350; 435/7.1; 435/69.1; 435/252.3; 435/320.1

(58) Field of Classification Search ......... 530/350, 530/380, 395; 435/7.1, 69.1, 252.3, 320.1
See application file for complete search history.

(56) References Cited

U.S. PATENT DOCUMENTS 6,476,195 B1 * 11/2002 Komatsoulis et al. ....... 530/350

FOREIGN PATENT DOCUMENTS

| WO | WO 99/14328 A2 | 3/1999 |
|----|----------------|--------|
| WO | WO 00/06698 A1 | 2/2000 |
| WO | WO 01/42285 A2 | 6/2001 |
| WO | WO 01/42285 A3 | 6/2001 |

OTHER PUBLICATIONS

Chen et al. "Amino acid sequence of protein PRO234." Database: A_Geneseq_Jun. 19, 2003; Accession No: AAY13367; Jun. 25, 1999.*

Rosen et al. as attachment.*

Borowsky, M.L. et al., "Layilin, a novel talin-binding transmembrane protein homologous with C-type lectins, is localized in membrane ruffles", *J Cell Biol* 143(2): 429-442, Oct. 19, 1998.

Bono, P. et al., "Layilin, a novel integral membrane protein, is a hyaluronan receptor", *Mol Biol Cell* 12: 891-900, Apr. 2001.

* cited by examiner

*Primary Examiner*—Jon Weber
*Assistant Examiner*—Rita Mitra
(74) *Attorney, Agent, or Firm*—Suzanne A. Sprunger; Susan E. Lingenfelter

(57) ABSTRACT

The invention is directed to purified and isolated novel ss3939 polypeptides, the nucleic acids encoding such polypeptides, processes for production of recombinant forms of such polypeptides, antibodies generated against these polypeptides, fragmented peptides derived from these polypeptides, and the uses of the above.

8 Claims, No Drawings

SEQUENCE LISTING

```
<160> NUMBER OF SEQ ID NOS: 9

<210> SEQ ID NO 1
<211> LENGTH: 2005
<212> TYPE: DNA
<213> ORGANISM: Homo sapiens

<400> SEQUENCE: 1
tgtcgcgcac gcctctgccc gccagcccgc tccaccgccg tagcgcccga gtgtcggggg      60
gcgcacccga gtcgggccat gaggccggga accgcgctac aggccgtgct gctggccgtg     120
ctgctggtgg ggctgcgggc cgcgacgggt cgcctgctga gtgggcagcc agtctgccgg     180
ggagggacac agaggccttg ttataaagtc atttacttcc atgatacttc tcgaagactg     240
aactttgagg aagccaaaga agcctgcagg agggatggag gccagctagt cagcatcgag     300
tctgaagatg aacagaaact gatagaaaag ttcattgaaa acctcttgcc atctgatggt     360
gacttctgga ttgggctcag gaggcgtgag gagaaacaaa gcaatagcac agcctgccag     420
gacctttatg cttggactga tggcagcata tcacaattta ggaactggta tgtggatgag     480
ccgtcctgcg gcagcgaggt ctgcgtggtc atgtaccatc agccatcggc acccgctggc     540 atcgaggcc cctacatgtt ccagtggaat gatgaccggt gcaacatgaa gaacaatttc     600
atttgcaaat attctgatga gaaaccagca gttccttcta gagaagctga aggtgaggaa     660
```

```
acagagctga caacacctgt acttccagaa gaaacacagg aagaagatgc caaaaaaaca    720
tttaaagaaa gtagagaagc tgccttgaat ctggcctaca tcctaatccc cagcattccc    780
cttctcctcc tccttgtggt caccacagtt gtatgttggg tttggatctg tagaaaaga    840 aaacgggagc agccagaccc tagcacaaag aagcaacaca ccatctggcc ctctcctcac    900
cagggaaaca gcccggacct agaggtctac aatgtcataa gaaaacaaag cgaagctgac    960
ttagctgaga cccggccaga cctgaagaat atttcattcc gagtgtgttc gggagaagcc   1020
actcccgatg acatgtcttg tgactatgac aacatggctg tgaacccatc agaaagtggg   1080
tttgtgactc tggtgagcgt ggagagtgga tttgtgacca atgacattta tgagttctcc   1140
ccagaccaaa tggggaggag taaggagtct ggatgggtgg aaaatgaaat atatggttat   1200
taggacatat aaaaaactga aactgacaac aatggaaaag aaatgataag caaaatcctc   1260
ttattttcta taaggaaaat acacagaagg tctatgaaca agcttagatc aggtcctgtg   1320
gatgagcatg tggtccccac gacctcctgt tggaccccca cgttttggct gtatcctta   1380 tcccagccag tcatccagct cgaccttatg agaaggtacc ttgcccaggt ctggcacata   1440
gtagagtctc aataaatgtc acttggttgg ttgtatctaa cttttaaggg acagagcttt   1500
acctggcagt gataaagatg ggctgtggag cttggaaaac cacctctgtt ttccttgctc   1560
tatacagcag cacatattat catacagaca gaaaatccag aatcttttca agcccacat    1620 atggtagcac aggttggcct gtgcatcggc aattctcata tctgtttttt tcaaagaata   1680
aaatcaaata aagagcagga acagagtgt tagtctgtgt ctacagccct tcctctgcat    1740
gtggccacag gggacctttt tttgtttctc ctgacatcca gacttggaaa tatctaacta   1800
cttgcaaaac taaaaatgag gccaggcgca gtggctgacg cctgtaatcc cagaaccttg   1860
ggagaccaag attggaggat agcttgagtt caggagttcc agaccttcct gggcaaaata   1920
gtgagactct gactctacaa aaaatttaaa aattagcagg gcatggtggc atgcgcctgc   1980
agtcccagct actcaggagg ccgag                                         2005

<210> SEQ ID NO 2
<211> LENGTH: 374
<212> TYPE: PRT
<213> ORGANISM: Homo sapiens

<400> SEQUENCE: 2

Met Arg Pro Gly Thr Ala Leu Gln Ala Val Leu Leu Ala Val Leu Leu
1               5                   10                  15

Val Gly Leu Arg Ala Ala Thr Gly Arg Leu Leu Ser Gly Gln Pro Val
                20                  25                  30

Cys Arg Gly Gly Thr Gln Arg Pro Cys Tyr Lys Val Ile Tyr Phe His
            35                  40                  45

Asp Thr Ser Arg Arg Leu Asn Phe Glu Glu Ala Lys Glu Ala Cys Arg
        50                  55                  60

Arg Asp Gly Gly Gln Leu Val Ser Ile Glu Ser Glu Asp Glu Gln Lys
65                  70                  75                  80

Leu Ile Glu Lys Phe Ile Glu Asn Leu Leu Pro Ser Asp Gly Asp Phe
                85                  90                  95

Trp Ile Gly Leu Arg Arg Arg Glu Glu Lys Gln Ser Asn Ser Thr Ala
                100                 105                 110

Cys Gln Asp Leu Tyr Ala Trp Thr Asp Gly Ser Ile Ser Gln Phe Arg
            115                 120                 125

Asn Trp Tyr Val Asp Glu Pro Ser Cys Gly Ser Glu Val Cys Val Val
```

```
            130                 135                 140
Met Tyr His Gln Pro Ser Ala Pro Ala Gly Ile Gly Gly Pro Tyr Met
145                 150                 155                 160

Phe Gln Trp Asn Asp Asp Arg Cys Asn Met Lys Asn Asn Phe Ile Cys
                165                 170                 175

Lys Tyr Ser Asp Glu Lys Pro Ala Val Pro Ser Arg Glu Ala Glu Gly
            180                 185                 190

Glu Glu Thr Glu Leu Thr Thr Pro Val Leu Pro Glu Thr Gln Glu
        195                 200                 205

Glu Asp Ala Lys Lys Thr Phe Lys Glu Ser Arg Glu Ala Ala Leu Asn
210                 215                 220

Leu Ala Tyr Ile Leu Ile Pro Ser Ile Pro Leu Leu Leu Leu Val
225                 230                 235                 240

Val Thr Thr Val Val Cys Trp Val Trp Ile Cys Arg Lys Arg Lys Arg
                245                 250                 255

Glu Gln Pro Asp Pro Ser Thr Lys Lys Gln His Thr Ile Trp Pro Ser
                260                 265                 270

Pro His Gln Gly Asn Ser Pro Asp Leu Glu Val Tyr Asn Val Ile Arg
            275                 280                 285

Lys Gln Ser Glu Ala Asp Leu Ala Glu Thr Arg Pro Asp Leu Lys Asn
        290                 295                 300

Ile Ser Phe Arg Val Cys Ser Gly Glu Ala Thr Pro Asp Asp Met Ser
305                 310                 315                 320

Cys Asp Tyr Asp Asn Met Ala Val Asn Pro Ser Glu Ser Gly Phe Val
                325                 330                 335

Thr Leu Val Ser Val Glu Ser Gly Phe Val Thr Asn Asp Ile Tyr Glu
            340                 345                 350

Phe Ser Pro Asp Gln Met Gly Arg Ser Lys Glu Ser Gly Trp Val Glu
        355                 360                 365

Asn Glu Ile Tyr Gly Tyr
    370

<210> SEQ ID NO 3
<211> LENGTH: 618
<212> TYPE: DNA
<213> ORGANISM: Homo sapiens

<400> SEQUENCE: 3
gcgacgggtc gcctgctgag tgggcagcca gtctgccggg gagggacaca gaggccttgt    60
tataaagtca tttacttcca tgatacttct cgaagactga actttgagga agccaaagaa   120
gcctgcagga gggatggagg ccagctagtc agcatcgagt ctgaagatga acagaaactg   180
atagaaaagt tcattgaaaa cctcttgcca tctgatggtg acttctggat tgggctcagg   240
aggcgtgagg agaaacaaag caatagcaca gcctgccagg acctttatgc ttggactgat   300
ggcagcatat cacaatttag gaactggtat gtggatgagc cgtcctgcgg cagcgaggtc   360
tgcgtggtca tgtaccatca gccatcggca cccgctggca tcggaggccc ctacatgttc   420
cagtggaatg atgaccggtg caacatgaag aacaatttca tttgcaaata ttctgatgag   480
aaaccagcag ttccttctag aagctgaagt ggtgaggaaa cagagctgac aacacctgta   540
cttccagaag aaacacagga agaagatgcc aaaaaaacat taaagaaagt agagaagct   600 gccttgaatc tggcctac                                                 618

<210> SEQ ID NO 4
```

<210> SEQ ID NO 4
<211> LENGTH: 378
<212> TYPE: DNA
<213> ORGANISM: Homo sapiens

<400> SEQUENCE: 4

```
tggatctgta gaaaagaaa acgggagcag ccagacccta gcacaaagaa gcaacacacc      60
atctggccct ctcctcacca gggaaacagc ccggacctag aggtctacaa tgtcataaga     120
aaacaaagcg aagctgactt agctgagacc cggccagacc tgaagaatat ttcattccga     180
gtgtgttcgg gagaagccac tcccgatgac atgtcttgtg actatgacaa catggctgtg     240
aacccatcag aaagtgggtt tgtgactctg gtgagcgtgg agagtggatt tgtgaccaat     300
gacatttatg agttctcccc agaccaaatg gggaggagta aggagtctgg atgggtggaa     360
aatgaaatat atggttat                                                   378
```

<210> SEQ ID NO 5
<211> LENGTH: 206
<212> TYPE: PRT
<213> ORGANISM: Homo sapiens

<400> SEQUENCE: 5

Ala Thr Gly Arg Leu Leu Ser Gly Gln Pro Val Cys Arg Gly Gly Thr
1               5                   10                  15

Gln Arg Pro Cys Tyr Lys Val Ile Tyr Phe His Asp Thr Ser Arg Arg
            20                  25                  30

Leu Asn Phe Glu Glu Ala Lys Glu Ala Cys Arg Arg Asp Gly Gly Gln
        35                  40                  45

Leu Val Ser Ile Glu Ser Glu Asp Glu Gln Lys Leu Ile Glu Lys Phe
    50                  55                  60

Ile Glu Asn Leu Leu Pro Ser Asp Gly Asp Phe Trp Ile Gly Leu Arg
65                  70                  75                  80

Arg Arg Glu Glu Lys Gln Ser Asn Ser Thr Ala Cys Gln Asp Leu Tyr
                85                  90                  95

Ala Trp Thr Asp Gly Ser Ile Ser Gln Phe Arg Asn Trp Tyr Val Asp
            100                 105                 110

Glu Pro Ser Cys Gly Ser Glu Val Cys Val Val Met Tyr His Gln Pro
        115                 120                 125

Ser Ala Pro Ala Gly Ile Gly Gly Pro Tyr Met Phe Gln Trp Asn Asp
    130                 135                 140

Asp Arg Cys Asn Met Lys Asn Asn Phe Ile Cys Lys Tyr Ser Asp Glu
145                 150                 155                 160

Lys Pro Ala Val Pro Ser Arg Glu Ala Glu Gly Glu Thr Glu Leu
                165                 170                 175

Thr Thr Pro Val Leu Pro Glu Glu Thr Gln Glu Glu Asp Ala Lys Lys
            180                 185                 190

Thr Phe Lys Glu Ser Arg Glu Ala Ala Leu Asn Leu Ala Tyr
        195                 200                 205

<210> SEQ ID NO 6
<211> LENGTH: 126
<212> TYPE: PRT
<213> ORGANISM: Homo sapiens

<400> SEQUENCE: 6

Trp Ile Cys Arg Lys Arg Lys Arg Glu Gln Pro Asp Pro Ser Thr Lys
1               5                   10                  15

Lys Gln His Thr Ile Trp Pro Ser Pro His Gln Gly Asn Ser Pro Asp

```
                    20                  25                  30
Leu Glu Val Tyr Asn Val Ile Arg Lys Gln Ser Glu Ala Asp Leu Ala
            35                  40                  45
Glu Thr Arg Pro Asp Leu Lys Asn Ile Ser Phe Arg Val Cys Ser Gly
 50                  55                  60
Glu Ala Thr Pro Asp Asp Met Ser Cys Asp Tyr Asp Asn Met Ala Val
 65                  70                  75                  80
Asn Pro Ser Glu Ser Gly Phe Val Thr Leu Val Ser Val Glu Ser Gly
                    85                  90                  95
Phe Val Thr Asn Asp Ile Tyr Glu Phe Ser Pro Asp Gln Met Gly Arg
                100                 105                 110
Ser Lys Glu Ser Gly Trp Val Glu Asn Glu Ile Tyr Gly Tyr
            115                 120                 125

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence:
      antigenic peptide used in fusion proteins

<400> SEQUENCE: 7

Asp Tyr Lys Asp Asp Asp Asp Lys
1               5

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence:  leucine
      zipper polypeptide

<400> SEQUENCE: 8

Pro Asp Val Ala Ser Leu Arg Gln Gln Val Glu Ala Leu Gln Gly Gln
1               5                  10                  15
Val Gln His Leu Gln Ala Ala Phe Ser Gln Tyr
            20                  25

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence:  leucine
      zipper polypeptide

<400> SEQUENCE: 9

Arg Met Lys Gln Ile Glu Asp Lys Ile Glu Glu Ile Leu Ser Lys Ile
1               5                  10                  15
Tyr His Ile Glu Asn Glu Ile Ala Arg Ile Lys Lys Leu Ile Gly Glu
            20                  25                  30
Arg
```

US 7,041,782 B2

LECTIN SS3939 DNA AND POLYPEPTIDES

This application is a continuation of U.S. application PCT/US99/30523, filed on Dec. 22, 1999; which claims the benefit under 35 USC 119(e) of provisional application U.S. Ser. No. 60/113,820, filed Dec. 23, 1998; all of which are incorporated by reference herein.

BACKGROUND OF THE INVENTION

1. Field of the Invention

The invention is directed to purified and isolated novel ss3939 polypeptides and fragments thereof, the nucleic acids encoding such polypeptides, processes for production of recombinant forms of such polypeptides, antibodies generated against these polypeptides, fragmented peptides derived from these polypeptides, and uses thereof.

2. Description of Related Art

Of recent interest are sugar-binding proteins, known as lectins, which mediate both pathogen recognition and cell-cell interactions using structurally related calcium-dependent carbohydrate-recognition domains, or C-type lectin domains (Drickamer, K. J., Biol. Chem. 263:9557–9560, 1988). In recognizing pathogens, certain C-lectin-containing proteins, such as the macrophage mannose receptor, bind terminal monosaccharide residues characteristic of fungal and bacterial cell surfaces (Fraser, I. P., Semin. Immunol., 10(5):363–72, 1988). The macrophage mannose receptor contains seven tandemly repeated C-type lectin domains, each of which consists of about 110 to 130 residues. There are four cysteines which are perfectly conserved and involved in two disulfide bonds.

The conserved size and amino acid composition of the C-type lectin domain provides a template for computer-based sequence comparison in the identification of novel sequences containing C-type lectin domains. Novel sequences encoding C-type lectin domains or domains similar to C-type lectin domains may have functions similar to those ascribed to previously described C-type lectin domain-containing molecules, such as recognizing, binding, and mediating the uptake of pathogens. The identification of novel molecules containing domains similar to the C-type lectin domain may thus lead to improved therapies for enhancing cellular immunity.

In addition, in view of the continuing interest in antigen recognition and the immune system, there is still a need in the art for the identity and function of proteins involved in cellular and immune responses.

In another aspect, the identification of the primary structure, or sequence, of an unknown protein is the culmination of an arduous process of experimentation. In order to identify an unknown protein, the investigator can rely upon a comparison of the unknown protein to known peptides using a variety of techniques known to those skilled in the art. For instance, proteins are routinely analyzed using techniques such as electrophoresis, sedimentation, chromatography, sequencing and mass spectrometry.

In particular, comparison of an unknown protein to polypeptides of known molecular weight allows a determination of the apparent molecular weight of the unknown protein (T. D. Brock and M. T. Madigan, Biology of Microorganisms, pp. 76–77, Prentice Hall, 6th ed., 1991). Protein molecular weight standards are commercially available to assist in the estimation of molecular weights of unknown protein (New England Biolabs Inc. Catalog:130–131, 1995; J. L. Hartley, U.S. Pat. No. 5,449,758). However, the molecular weight standards may not correspond closely enough in size to the unknown protein to allow an accurate estimation of apparent molecular weight. The difficulty in estimation of molecular weight is compounded in the case of proteins that are subjected to fragmentation by chemical or enzymatic means, modified by post-translational modification or processing, and/or associated with other proteins in non-covalent complexes.

In addition, the unique nature of the composition of a protein with regard to its specific amino acid constituents results in unique positioning of cleavage sites within the protein. Specific fragmentation of a protein by chemical or enzymatic cleavage results in a unique "peptide fingerprint" (D. W. Cleveland et al., J. Biol. Chem. 252:1102–1106, 1977; M. Brown et al., J. Gen. Virol. 50:309–316, 1980). Consequently, cleavage at specific sites results in reproducible fragmentation of a given protein into peptides of precise molecular weights. Furthermore, these peptides possess unique charge characteristics that determine the isoelectric pH of the peptide. These unique characteristics can be exploited using a variety of electrophoretic and other techniques (T. D. Brock and M. T. Madigan, Biology of Microorganisms, pp. 76–77, Prentice Hall, 6th ed. 1991).

Fragmentation of proteins is further employed for amino acid composition analysis and protein sequencing (P. Matsudiara, J. Biol. Chem. 262:10035–10038, 1987; C. Eckerskorn et al., Electrophoresis, 9:830–838, 1988), particularly the production of fragments from proteins with a "blocked" N-terminus. In addition, fragmented proteins can be used for immunization, for affinity selection (R. A. Brown, U.S. Pat. No. 5,151,412), for determination of modification sites (e.g. phosphorylation), for generation of active biological compounds (T. D. Brock and M. T. Madigan, Biology of Microorganisms, pp. 300–301, Prentice Hall, 6th ed. 1991), and for differentiation of homologous proteins (M. Brown et al., J. Gen. Virol. 50:309–316, 1980).

In addition, when a peptide fingerprint of an unknown protein is obtained, it can be compared to a database of known proteins to assist in the identification of the unknown protein using mass spectrometry (W. J. Henzel et al., Proc. Natl. Acad. Sci. USA 90:5011–5015, 1993; D. Fenyo et al., Electrophoresis 19:998–1005, 1998). A variety of computer software programs to facilitate these comparisons are accessible via the Internet, such as Protein Prospector (Internet site: prospector.uscf.edu), MultiIdent (Internet site: www.expasy.ch/sprot/multiident.html), PeptideSearch (Internet site: www.mann.embl-heiedelberg.de...deSearch/FR_PeptideSearch Form.html), and ProFound (Internet site: www.chait-sgi.rockefeller.edu/cgi-bin/prot-id-frag.html). These programs allow the user to specify the cleavage agent and the molecular weights of the fragmented peptides within a designated tolerance. The programs compare these molecular weights to protein molecular weight information stored in databases to assist in determining the identity of the unknown protein. Accurate information concerning the number of fragmented peptides and the precise molecular weight of those peptides is required for accurate identification. Therefore, increasing the accuracy in determining the number of fragmented peptides and their molecular weight should result in enhanced likelihood of success in the identification of unknown proteins.

In addition, peptide digests of unknown proteins can be sequenced using tandem mass spectrometry (MS/MS) and the resulting sequence searched against databases (J. K. Eng et al., J. Am. Soc. Mass Spec. 5:976–989, 1994; M. Mann et al., Anal. Chem. 66:4390–4399, 1994; J. A. Taylor et al., Rapid Comm. Mass Spec. 11:1067–1075, 1997). Searching programs that can be used in this process exist on the Internet, such as Lutefisk 97 (Internet site: www.lsbc.com: 70/Lutefisk97.html), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Thus, there also exists a need in the art for polypeptides suitable for use in peptide fragmentation studies, for use in molecular weight measurements, and for use in protein sequencing using tandem mass spectrometry.

SUMMARY OF THE INVENTION

The invention aids in fulfilling these various needs in the art by providing isolated, novel polypeptides, termed "ss3939." Specifically, this invention provides the nucleic acids for ss3939 and polypeptides encoded by these nucleic acids. Particular embodiments of the invention are directed to an isolated ss3939 nucleic acid molecule comprising the DNA sequence of SEQ ID NO:1 and an isolated ss3939 nucleic acid molecule encoding the amino acid sequence of SEQ ID NO:2, as well as nucleic acid molecules complementary to these sequences.

Both single-stranded and double-stranded RNA and DNA nucleic acid molecules are encompassed by the invention, as well as nucleic acid molecules that hybridize to a denatured, double-stranded DNA comprising all or a portion of SEQ ID NO:1 and/or SEQ ID NO:2. Also encompassed are isolated nucleic acid molecules that are derived by in vitro mutagenesis of nucleic acid molecules comprising sequences of SEQ ID NO:1, that are degenerate from nucleic acid molecules comprising sequences of SEQ ID NO:1, and that are allelic variants of DNA of the invention. The invention also encompasses recombinant vectors that direct the expression of these nucleic acid molecules and host cells stably or transiently transformed or transfected with these vectors.

In addition, the invention encompasses methods of using the nucleic acids noted above to identify nucleic acids encoding proteins bearing the C-type lectin domain (such as members of the mannose receptor family); to identify human chromosome number 11; to map genes on human chromosome number 11; to identify genes associated with certain diseases, syndromes, or other human conditions associated with human chromosome number 11; and to study antigen recognition, capture, and uptake; non-adaptive host responses to infection; and the immune system, in particular dendritic cell function.

The invention also encompasses the use of sense or antisense oligonucleotides from the nucleic acid of SEQ ID NO:1 to inhibit the expression of the polynucleotide encoded by the ss3939 gene.

The invention also encompasses isolated polypeptides and fragments thereof encoded by these nucleic acid molecules including soluble polypeptide portions of SEQ ID NO:2. The invention further encompasses methods for the production of these polypeptides, including culturing a host cell under conditions promoting expression and recovering the polypeptide from the culture medium. Especially, the expression of these polypeptides in bacteria, yeast, plant, insect, and animal cells is encompassed by the invention.

In general, the polypeptides of the invention can be used to study cellular processes such as responses to infection, antigen capture, cell proliferation, cell death, cell migration, cell-to-cell interaction, and inflammatory responses. In one aspect, the polypeptides of the invention can be used for the study of signal transduction. In addition, these polypeptides can be used to identify proteins associated with ss3939 polypeptides.

In addition, the invention includes assays utilizing these polypeptides to screen for potential inhibitors of activity associated with polypeptide counter-structure molecules, and methods of using these polypeptides as therapeutic agents for the treatment of diseases mediated by ss3939 polypeptide counter-structure molecules. Further, methods of using these polypeptides in the design of inhibitors thereof are also an aspect of the invention.

The invention further provides a method for using these polypeptides as molecular weight markers that allow the estimation of the molecular weight of a protein or a fragmented protein, as well as a method for the visualization of the molecular weight markers of the invention thereof using electrophoresis. The invention further encompasses methods for using the polypeptides of the invention as markers for determining the isoelectric point of an unknown protein, as well as controls for establishing the extent of fragmentation of a protein.

Further encompassed by this invention are kits to aid in these determinations.

Further encompassed by this invention is the use of the ss3939 nucleic acid sequences, predicted amino acid sequences of the polypeptide or fragments thereof, or a combination of the predicted amino acid sequences of the polypeptide and fragments thereof for use in searching an electronic database to aid in the identification of sample nucleic acids and/or proteins.

Isolated polyclonal or monoclonal antibodies that bind to these polypeptides are also encompassed by the invention, in addition to the use of these antibodies for purifying the ss3939 polypeptide and for inhibiting or promoting ss3939 or binding partner signal transduction.

DETAILED DESCRIPTION OF THE INVENTION

The nucleic acid molecules encompassed in the invention include the following nucleotide sequences:

```
Name: ss3939

1 TGTCGCGCAC GCCTCTGCCC GCCAGCCCGC TCCACCGCCG TAGCGCCCGA (SEQ ID NO:1)

51 GTGTCGGGGG GCGCACCCGA GTCGGGCCAT GAGGCCGGGA ACCGCGCTAC

101 AGGCCGTGCT GCTGGCCGTG CTGCTGGTGG GGCTGCGGGC CGCGACGGGT

151 CGCCTGCTGA GTGGGCAGCC AGTCTGCCGG GGAGGGACAC AGAGGCCTTG

201 TTATAAAGTC ATTTACTTCC ATGATACTTC TCGAAGACTG AACTTTGAGG
```

-continued

```
 251 AAGCCAAAGA AGCCTGCAGG AGGGATGGAG GCCAGCTAGT CAGCATCGAG

301 TCTGAAGATG AACAGAAACT GATAGAAAAG TTCATTGAAA ACCTCTTGCC

351 ATCTGATGGT GACTTCTGGA TTGGGCTCAG GAGGCGTGAG GAGAAACAAA

401 GCAATAGCAC AGCCTGCCAG GACCTTTATG CTTGGACTGA TGGCAGCATA

451 TCACAATTTA GGAACTGGTA TGTGGATGAG CCGTCCTGCG GCAGCGAGGT

501 CTGCGTGGTC ATGTACCATC AGCCATCGGC ACCCGCTGGC ATCGGAGGCC

551 CCTACATGTT CCAGTGGAAT GATGACCGGT GCAACATGAA GAACAATTTC

601 ATTTGCAAAT ATTCTGATGA GAAACCAGCA GTTCCTTCTA GAGAAGCTGA

651 AGGTGAGGAA ACAGAGCTGA CAACACCTGT ACTTCCAGAA GAAACACAGG

701 AAGAAGATGC CAAAAAAACA TTTAAAGAAA GTAGAGAAGC TGCCTTGAAT

751 CTGGCCTACA TCCTAATCCC CAGCATTCCC CTTCTCCTCC TCCTTGTGGT

801 CACCACAGTT GTATGTTGGG TTTGGATCTG TAGAAAAAGA AAACGGGAGC

851 AGCCAGACCC TAGCACAAAG AAGCAACACA CCATCTGGCC CTCTCCTCAC

901 CAGGGAAACA GCCCGGACCT AGAGGTCTAC AATGTCATAA GAAAACAAAG

951 CGAAGCTGAC TTAGCTGAGA CCCGGCCAGA CCTGAAGAAT ATTTCATTCC

1001 GAGTGTGTTC GGGAGAAGCC ACTCCCGATG ACATGTCTTG TGACTATGAC

1051 AACATGGCTG TGAACCCATC AGAAAGTGGG TTTGTGACTC TGGTGAGCGT

1101 GGAGAGTGGA TTTGTGACCA ATGACATTTA TGAGTTCTCC CCAGACCAAA

1151 TGGGGAGGAG TAAGGAGTCT GGATGGGTGG AAAATGAAAT ATATGGTTAT

1201 TAGGACATAT AAAAAACTGA AACTGACAAC AATGGAAAAG AAATGATAAG

1251 CAAAATCCTC TTATTTTCTA TAAGGAAAAT ACACAGAAGG TCTATGAACA

1301 AGCTTAGATC AGGTCCTGTG GATGAGCATG TGGTCCCCAC GACCTCCTGT

1351 TGGACCCCCA CGTTTTGGCT GTATCCTTTA TCCCAGCCAG TCATCCAGCT

1401 CGACCTTATG AGAAGGTACC TTGCCCAGGT CTGGCACATA GTAGAGTCTC

1451 AATAAATGTC ACTTGGTTGG TTGTATCTAA CTTTTAAGGG ACAGAGCTTT

1501 ACCTGGCAGT GATAAAGATG GGCTGTGGAG CTTGGAAAAC CACCTCTGTT

1551 TTCCTTGCTC TATACAGCAG CACATATTAT CATACAGACA GAAAATCCAG

1601 AATCTTTTCA AAGCCCACAT ATGGTAGCAC AGGTTGGCCT GTGCATCGGC

1651 AATTCTCATA TCTGTTTTTT TCAAAGAATA AAATCAAATA AAGAGCAGGA

1701 AACAGAGTGT TAGTCTGTGT CTACAGCCCT TCCTCTGCAT GTGGCCACAG

1751 GGGACCTTTT TTTGTTTCTC CTGACATCCA GACTTGGAAA TATCTAACTA

1801 CTTGCAAAAC TAAAAATGAG GCCAGGCGCA GTGGCTGACG CCTGTAATCC

1851 CAGAACCTTG GGAGACCAAG ATTGGAGGAT AGCTTGAGTT CAGGAGTTCC

1901 AGACCTTCCT GGGCAAAATA GTGAGACTCT GACTCTACAA AAAATTTAAA

1951 AATTAGCAGG GCATGGTGGC ATGCGCCTGC AGTCCCAGCT ACTCAGGAGG

2001 CCGAG
```

Additional preferred nucleotide sequences of the invention include:
the extracellular coding domain (nucleotides 142–759):

nt142

```
 GCGACGGGT CGCCTGCTGA GTGGGCAGCC AGTCTGCCGG GGAGGGACAC (SEQ ID NO:3)
AGAGGCCTTG TTATAAAGTC ATTTACTTCC ATGATACTTC TCGAAGACTG
AACTTTGAGG AAGCCAAAGA AGCCTGCAGG AGGGATGGAG GCCAGCTAGT
CAGCATCGAG TCTGAAGATG AACAGAAACT GATAGAAAAG TTCATTGAAA
ACCTCTTGCC ATCTGATGGT GACTTCTGGA TTGGGCTCAG GAGGCGTGAG
GAGAAACAAA GCAATAGCAC AGCCTGCCAG GACCTTTATG CTTGGACTGA
TGGCAGCATA TCACAATTTA GGAACTGGTA TGTGGATGAG CCGTCCTGCG
GCAGCGAGGT CTGCGTGGTC ATGTACCATC AGCCATCGGC ACCCGCTGGC
ATCGGAGGCC CCTACATGTT CCAGTGGAAT GATGACCGGT GCAACATGAA
GAACAATTTC ATTTGCAAAT ATTCTGATGA GAAACCAGCA GTTCCTTCTA
GAGAAGCTGA AGGTGAGGAA ACAGAGCTGA CAACACCTGT ACTTCCAGAA
GAAACACAGG AAGAAGATGC CAAAAAAACA TTTAAAGAAA GTAGAGAAGC
TGCCTTGAAT CTGGCCTAC nt759
``` and the cytoplasmic or intracellular domain (nucleotides 823–1200):

nt823

```
   TGGATCTG TAGAAAAAGA AAACGGGAGC AGCCAGACCC TAGCACAAAG (SEQ ID NO:4)
AAGCAACACA CCATCTGGCC CTCTCCTCAC CAGGGAAACA GCCCGGACCT
AGAGGTCTAC AATGTCATAA GAAAACAAAG CGAAGCTGAC TTAGCTGAGA
CCCGGCCAGA CCTGAAGAAT ATTTCATTCC GAGTGTGTTC GGGAGAAGCC
ACTCCCGATG ACATGTCTTG TGACTATGAC AACATGGCTG TGAACCCATC
AGAAAGTGGG TTTGTGACTC TGGTGAGCGT GGAGAGTGGA TTTGTGACCA
ATGACATTTA TGAGTTCTCC CCAGACCAAA TGGGGAGGAG TAAGGAGTCT
GGATGGGTGG AAAATGAAAT ATATGGTTAT nt1200
```

The amino acid sequences of the polypeptides encoded by the nucleotide sequence of the invention includes:

Name: ss3939 (polypeptide)

```
  1 MRPGTALQAV LLAVLLVGLR AATGRLLSGQ PVCRGGTQRP CYKVIYFHDT (SEQ ID NO:2)

51 SRRLNFEEAK EACRRDGGQL VSIESEDEQK LIEKFIENLL PSDGDFWIGL

101 RRREEKQSNS TACQDLYAWT DGSISQFRNW YVDEPSCGSE VCVVMYHQPS

151 APAGIGGPYM FQWNDDRCNM KNNFICKYSD EKPAVPSREA EGEETELTTP

201 VLPEETQEED AKKTFKESRE AALNLAYILI PSIPLLLLLV VTTVVCWVWI

251 CRKRKREQPD PSTKKQHTIW PSPHQGNSPD LEVYNVIRKQ SEADLAETRP
```

-continued

```
301 DLKNISFRVC SGEATPDDMS CDYDNMAVNP SESGFVTLVS VESGFVTNDI

351 YEFSPDQMGR SKESGWVENE IYGY
```

Additional preferred polypeptide sequences of the invention include:
the extracellular domain (amino acids 22–227)

```
aa22

ATGRLLSGQ PVCRGGTQRP CYKVIYFHDT SRRLNFEEAK EACRRDGGQL  (SEQ ID NO:5)

VSIESEDEQK LIEKFIENLL PSDGDFWIGL RRREEKQSNS TACQDLYAWT

DGSISQFRNW YVDEPSCGSE VCVVMYHQPS APAGIGGPYM FQWNDDRCNM

KNNFICKYSD EKPAVPSREA EGEETELTTP VLPEETQEED AKKTFKESRE

AALNLAY aa227
``` and
the intracellular domain (amino acids 249–374)

```
aa249

WI CRKRKREQPD PSTKKQHTIW PSPHQGNSPD LEVYNVIRKQ  (SEQ ID NO:6)

SEADLAETRP DLKNISFRVC SGEATPDDMS CDYDNMAVNP SESGFVTLVS

VESGFVTNDI YEFSPDQMGR SKESGWVENE IYGY aa374
```

The discovery of the nucleic acids of the invention enables the construction of expression vectors comprising nucleic acid sequences encoding polypeptides; host cells transfected or transformed with the expression vectors; isolated and purified biologically active polypeptides and fragments thereof; the use of the nucleic acids or oligonucleotides thereof as probes to identify nucleic acids encoding proteins having C-type lectin domains (such as those of the mannose receptor family); the use of the nucleic acids or oligonucleotides thereof to identify human chromosome number 11; the use of the nucleic acids or oligonucleotides thereof to map genes on human chromosome number 11; the use of the nucleic acid or oligonucleotides thereof to identify genes associated with certain diseases, syndromes or other human conditions associated with human chromosome number 11, including a rare form of diabetes mellitus, familial hyperproinsulinemia, sickle cell anemia, anal canal carcinoma and breast cancer; the use of single-stranded sense or antisense oligonucleotides from the nucleic acids to inhibit expression of polynucleotide encoded by the ss3939 gene; the use of such polypeptides and soluble fragments to bind ligands, for example polysaccharide moieties; the use of such polypeptides and fragmented peptides as molecular weight markers; the use of such polypeptides and fragmented peptides as controls for peptide fragmentation, and kits comprising these reagents; the use of such polypeptides and fragments thereof to generate antibodies; and the use of antibodies for purifying the ss3939 polypeptide and for inhibiting or promoting ss3939 or binding partner signal transduction.

Nucleic Acid Molecules

In a particular embodiment, the invention relates to certain isolated nucleotide sequences that are free from contaminating endogenous material. A "nucleotide sequence" refers to a polynucleotide molecule in the form of a separate fragment or as a component of a larger nucleic acid construct. The nucleic acid molecule has been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y., 1989). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Nucleic acid molecules of the invention include DNA in both single-stranded and double-stranded form, as well as the RNA complement thereof. DNA includes, for example, cDNA, genomic DNA, chemically synthesized DNA, DNA amplified by PCR, and combinations thereof. Genomic DNA may be isolated by conventional techniques, e.g., using the cDNA of SEQ ID NO:1, or a suitable fragment thereof, as a probe.

The DNA molecules of the invention include full length genes as well as polynucleotides and fragments thereof. The full length gene may include the N-terminal signal peptide.

Other embodiments include DNA encoding a soluble form, e.g., encoding the extracellular domain of the protein, either with or without the signal peptide.

The nucleic acids of the invention are preferentially derived from human sources, but the invention includes those derived from non-human species, as well.

Preferred Sequences

A preferred nucleotide sequence of the invention is SEQ ID NO:1, as set forth above, particularly nucleotides 79–1200 which encode the predicted full length translation product (amino acids 1–374 of SEQ ID NO:2). Nucleotides 79 to 141 encode the predicted signal sequence (amino acids 1–21), although alternative signal sequences may encompass nucleotides 79 to 147 (amino acids 1–23) or nucleotides 79 to 150 (amino acids 1–24). Nucleotides 142 to 759 encode the predicted extracellular coding domain (amino acids 22 to 227), with nucleotides 148 to 759 (amino acids 24 to 227) and 151 to 759 (amino acids 25 to 227) as possible alternatives. Nucleotides 760 to 822 encode the predicted transmembrane domain (amino acids 228–248) with nucleotides 823 to 1200 encoding the predicted cytoplasmic or intracellular domain (amino acids 249–374).

A cDNA clone having the nucleotide sequence of SEQ ID NO:1 was isolated as described in Example 1. The sequence of amino acids encoded by the DNA of SEQ ID NO:1 is shown in SEQ ID NO:2. Portions of the predicted ss3939 extracellular domain are homologous or similar to C-type lectin domains, such as those contained in the macrophage mannose receptor.

Additional Sequences

Due to the known degeneracy of the genetic code, wherein more than one codon can encode the same amino acid, a DNA sequence can vary from that shown in SEQ ID NO:1, and still encode a polypeptide having the amino acid sequence of SEQ ID NO:2. Such variant DNA sequences can result from silent mutations (e.g., occurring during PCR amplification), or can be the product of deliberate mutagenesis of a native sequence.

The invention thus provides isolated DNA sequences encoding polypeptides of the invention, selected from: (a) DNA comprising the nucleotide sequence of SEQ ID NO:1; (b) DNA encoding the polypeptide of SEQ ID NO:2; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

As used herein, conditions of moderate stringency can be readily determined by those having ordinary skill in the art based on, for example, the length of the DNA. The basic conditions are set forth by Sambrook et al., *Molecular Cloning: A Laboratory Manual,* 2nd ed. Vol. 1, pp. 1.101–104, Cold Spring Harbor Laboratory Press, 1989, and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Also included as an embodiment of the invention is DNA encoding polypeptide fragments and polypeptides comprising inactivated N-glycosylation site(s), inactivated protease processing site(s), or conservative amino acid substitution (s), as described below.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence.

The percent identity may be determined by visual inspection and mathematical calculation. Alternatively, the percent identity of two nucleic acid sequences can be determined by comparing sequence information using the GAP computer program, version 6.0 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps. Other programs used by one skilled in the art of sequence comparison may also be used.

The invention also provides isolated nucleic acids useful in the production of polypeptides. Such polypeptides may be prepared by any of a number of conventional techniques. A DNA sequence encoding an ss3939 polypeptide, or desired fragment thereof may be subcloned into an expression vector for production of the polypeptide or fragment. The DNA sequence advantageously is fused to a sequence encoding a suitable leader or signal peptide. Alternatively, the desired fragment may be chemically synthesized using known techniques. DNA fragments also may be produced by restriction endonuclease digestion of a full length cloned DNA sequence, and isolated by electrophoresis on agarose gels. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

The well-known polymerase chain reaction (PCR) procedure also may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., *Science* 239:487, 1988; Wu et al. eds., *Recombinant DNA Methodology,* pp. 189–196, Academic Press, Inc., San Diego, 1989; and Innis et al. eds., *PCR Protocols: A Guide to Methods and Applications,* Academic Press, Inc., 1990.

Polypeptides and Fragments Thereof

The invention encompasses polypeptides and fragments thereof in various forms, including those that are naturally occurring or produced through various techniques such as procedures involving recombinant DNA technology. Such forms include, but are not limited to, derivatives, variants, and oligomers, as well as fusion proteins or fragments thereof.

Polypeptides and Fragments Thereof

The polypeptides of the invention include full length proteins (amino acids 1–374) encoded by the nucleic acid sequences set forth above. Particularly preferred polypeptides comprise the amino acid sequence of SEQ ID NO:2 with particularly preferred fragments comprising amino acids 22 to 227 of SEQ ID NO:2. In general, fragments comprise at least 20, or at least 30, contiguous amino acids of the sequence of SEQ ID NO:2.

The polypeptide of SEQ ID NO:2 includes an N-terminal hydrophobic region that functions as a signal peptide, followed by an extracellular domain comprising amino acids 22 to 227, a transmembrane region comprising amino acids 228 through 248, and a C-terminal cytoplasmic domain comprising amino acids 249 to 374. Computer analysis predicts that the signal peptide corresponds to residues 1 to 21 of SEQ ID NO:2 (although the next most likely computer-predicted signal peptide cleavage sites (in descending order) occur after amino acids 24 and 23 of SEQ ID NO:2). Thus, cleavage of the signal peptide would yield a mature protein comprising amino acids 22 through 374 of SEQ ID NO:2. Cleavage at alternative sites may yield a mature protein comprising amino acids 25 through 374 and 24 through 374 of SEQ ID NO:2.

The skilled artisan will recognize that the above-described boundaries of such regions of the polypeptide are approximate and that the boundaries of the transmembrane region (which may be predicted by using computer programs available for that purpose) may differ from those described above.

The polypeptides of the invention may be membrane bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide. The presence of polypeptide in the medium indicates that the polypeptide was secreted from the cells and thus is a soluble form of the protein.

In one embodiment, the soluble polypeptides and fragments thereof comprise all or part of the extracellular domain, but lack the transmembrane region that would cause retention of the polypeptide on a cell membrane. A soluble polypeptide may also include the cytoplasmic domain, or a portion thereof, as long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain a desired biological activity. Particular embodiments are directed to polypeptide fragments that retain the ability to bind ss3939 binding partners such as polysaccharide moieties. Such a fragment may be a soluble polypeptide, as described above. In another embodiment, the polypeptides and fragments advantageously include regions that are conserved in the mannose receptor family as described above.

The invention also provides polypeptide fragments comprising at least 20, or at least 30, contiguous amino acids of SEQ ID NO:2. Fragments derived from the cytoplasmic domain of ss3939 find use in studies of signal transduction and in regulating cellular responses associated with transduction of biological signals. Other polypeptide fragments, particularly those derived from the extracellular domain of SEQ ID NO:2, can be used as immunogens, in generating antibodies against ss3939.

Variants

Naturally occurring variants as well as derived variants of the polypeptides and fragments are provided herein.

Variants may exhibit amino acid sequences that are at least 80% identical. Also contemplated are embodiments in which a polypeptide or fragment comprises an amino acid sequence that is at least 90% identical, at least 95% identical, at least 98% identical, at least 99% identical, or at least 99.9% identical to the preferred polypeptide or fragment thereof. Percent identity may be determined by visual inspection and mathematical calculation. Alternatively, the percent identity of two protein sequences can be determined by comparing sequence information using the GAP computer program, based on the algorithm of Needleman and Wunsch, *J. Mol. Bio.*, 48:443, 1970, and available from the University of Wisconsin Genetics Computer Group (UWGCG). The preferred default parameters for the GAP program include: (1) a scoring matrix, blosum62, as described by Henikoff and Henikoff, *Proc. Natl. Acad. Sci. USA*, 89:10915, 1992, (2) a gap weight of 12; (3) a gap length weight of 4; and (4) no penalty for end gaps. Other programs used by one skilled in the art of sequence comparison may also be used.

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1–5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregative conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalent or aggregative conjugates of the polypeptides with other proteins or polypeptides, such as by synthesis in recombinant culture as N-terminal or C-terminal fusions. Examples of fusion proteins are discussed below in connection with oligomers. Further, fusion proteins can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO:7), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native polypeptides that retain the native biological activity or the substantial equivalent thereof. One example is a variant that binds with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known.

Similarly, the DNAs of the invention include variants that differ from a native DNA sequence because of one or more deletions, insertions or substitutions, but that encode a biologically active polypeptide.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of polypeptides of the invention in bacterial expression systems, such as *E. coli*, provides non-glycosylated molecules. Further, a given preparation may include multiple differentially glycosylated species of the protein. Glycosyl groups can be removed through conventional methods, in particular those utilizing glycopeptidase. In general, glycosylated polypeptides of the invention can be incubated with a molar excess of glycopeptidase (Boehringer Mannheim).

Correspondingly, similar DNA constructs that encode various additions or substitutions of amino acid residues or sequences, or deletions of terminal or internal residues or sequences are encompassed by the invention. For example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in proteins include those described in U.S. Pat. No. 5,071,972 and EP 276,846, hereby incorporated by reference.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation.

Other variants are prepared by modification of adjacent dibasic amino acid residues, to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers or fusion proteins that contain ss3939 polypeptides. When the polypeptide of the invention is a type I membrane protein, such as ss3939, the fusion partner is linked to the C terminus of the type I membrane protein. Such fusion oligomers may be in the form of covalently-linked or non-covalently-linked multimers, including dimers, trimers, or higher oligomers. As noted above, preferred polypeptides are soluble and thus these oligomers may comprise soluble polypeptides. In one aspect of the invention, the oligomers maintain the binding ability of the polypeptide components and provide therefor, bivalent, trivalent, etc., binding sites.

One embodiment of the invention is directed to oligomers comprising multiple polypeptides joined via covalent or non-covalent interactions between peptide moieties fused to the polypeptides. Such peptides may be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Immunoglobulin-based Oligomers

As one alternative, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., *Proc. Natl. Acad. Sci. USA*, 88:10535, 1991; Byrn et al., *Nature* 344:677, 1990; and Hollenbaugh and Aruffo, "Construction of Immunoglobulin Fusion Proteins," in *Current Protocols in Immunology*, Suppl. 4, pages 10.19.1–10.19.11, 1992.

One embodiment of the present invention is directed to a dimer comprising two fusion proteins created by fusing a polypeptide of the invention to an Fc polypeptide derived from an antibody. A gene fusion encoding the polypeptide/Fc fusion protein is inserted into an appropriate expression vector. Polypeptide/Fc fusion proteins are expressed in host cells transformed with the recombinant expression vector, and allowed to assemble much like antibody molecules, whereupon interchain disulfide bonds form between the Fc moieties to yield divalent molecules.

The term "Fc polypeptide" as used herein includes native and mutein forms of polypeptides made up of the Fe region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., *EMBO J.* 13:3992–4001, 1994, incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible to form an oligomer with as many as four ss3939 extracellular regions.

Peptide-linker Based Oligomers

Alternatively, the oligomer is a fusion protein comprising multiple polypeptides, with or without peptide linkers (spacer peptides). Among the suitable peptide linkers are those described in U.S. Pat. Nos. 4,751,180 and 4,935,233, which are hereby incorporated by reference. A DNA sequence encoding a desired peptide linker may be inserted between, and in the same reading frame as, the DNA sequences of the invention, using any suitable conventional technique. For example, a chemically synthesized oligonucleotide encoding the linker may be ligated between the sequences. In particular embodiments, a fusion protein comprises from two to four soluble ss3939 polypeptides, separated by peptide linkers.

Leucine-Zippers

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240: 1759, 1988). The products of the nuclear oncogenes fos and jun comprise zipper domains that preferentially form heterodimer (O'Shea et al., *Science* 245:646, 1989; and Turner et al., *Science* 243:1689, 1989). The zipper domain is necessary for biological activity (DNA binding) in these proteins.

The fusogenic proteins of several different viruses, including paramyxovirus, coronavirus, measles virus and many retroviruses, also possess zipper domains (Buckland et al., *Nature* 338:547, 1989; Britton, *Nature* 353:394, 1991; Delwart et al., *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al, *Proc. Natl. Acad. Sci. U.S.A.* 88:3523, 1991). Zipper domains have also been recently reported to play a role in oligomerization of heat-shock transcription factors (Rabindran et al., *Science* 259: 230, 1993).

Zipper domains fold as short, parallel coiled coils (O'Shea et al., *Science* 254:539; 1991). The general architecture of the parallel coiled coil has been well characterized, with a "knobs-into-holes" packing as proposed by Crick in 1953 (Crick, *Acta Crystallogr.* 6:689, 1953). The dimer formed by a zipper domain is stabilized by the heptad repeat, designated (abcdefg), according to the notation of McLachlan et al., *J. Mol. Biol.* 98:293, 1975, in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek et al., *Int. J. Peptide Res.* 38:229, 1991). Lovejoy et al., *Science* 259:1288, 1993, recently reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Further discussion of the structure of leucine zippers is found in Harbury et al., *Science* 262:1401, 1993.

Examples of leucine zipper domains suitable for producing soluble oligomeric proteins are described in PCT application WO 94/10308, as well as the leucine zipper derived from lung surfactant protein D (SPD) described in Hoppe et al., *FEBS Letters* 344:191, 1994, hereby incorporated by reference. The use of a modified leucine zipper that allows for stable trimerization of a heterologous protein fused thereto is described in Fanslow et al., *Semin. Immunol.* 6:267–278, 1994. Recombinant fusion proteins comprising a soluble polypeptide fused to a leucine zipper peptide are expressed in suitable host cells, and the soluble oligomer that forms is recovered from the culture supernatant.

Certain leucine zipper moieties preferentially form trimers. One example is a leucine zipper derived from lung surfactant protein D (SPD) noted above, as described in Hoppe et al., *FEBS Letters* 344:191, 1994 and in U.S. Pat. No. 5,716,805, hereby incorporated by reference in their entirety. This lung SPD-derived leucine zipper peptide comprises the amino acid sequence Pro Asp Val Ala Ser Leu Arg Gln Gln Val Glu Ala Leu Gln Gly Gln Val Gln His Leu Gln Ala Ala Phe Ser Gln Tyr (SEQ ID NO:8).

Another example of a leucine zipper that promotes trimerization is a peptide comprising the amino acid sequence Arg Met Lys Gln Ile Glu Asp Lys Ile Glu Glu Ile Leu Ser Lys Ile Tyr His Ile Glu Asn Glu Ile Ala Arg Ile Lys Lys Leu Ile Gly Glu Arg (SEQ ID NO:9), as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained.

Other peptides derived from naturally occurring trimeric proteins may be employed in preparing trimeric ss3939 polypeptides. Alternatively, synthetic peptides that promote oligomerization may be employed. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Production of Polypeptides and Fragments Thereof

Expression, isolation and purification of the polypeptides and fragments of the invention may be accomplished by any suitable technique, including but not limited to the following:

Expression Systems

The present invention also provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site. Particular embodiments of mature proteins provided herein include, but are not limited to, proteins having the residue at position 22, 25, or 26 of SEQ ID NO:2 as the N-terminal amino acid.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, New York, 1985. Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, p. 412, Cold Spring Harbor Laboratory, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al., *J. Biol. Chem.* 258:2674, 1982; and Beier et al., *Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. (Kurjan et al., *Cell* 30:933, 1982; and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47, 1988. Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al., *EMBO J.* 10: 2821, 1991.

Established methods for introducing DNA into mammalian cells have been described (Kaufman, R. J., *Large Scale Mammalian Cell Culture*, pp. 15–69,1990). Additional protocols using commercially available reagents, such as Lipofectamine lipid reagent (Gibco/BRL) or Lipofectamine-Plus lipid reagent, can be used to transfect cells (Felgner et al., *Proc. Natl. Acad. Sci. USA* 84:7413–7417, 1987). In addition, electroporation can be used to transfect mammalian cells using conventional procedures, such as those in Sambrook et al., *Molecular Cloning: A Laboratory Manual*, 2nd ed. Vol. 1–3, Cold Spring Harbor Laboratory Press, 1989. Selection of stable transformants can be performed using methods known in the art, such as, for example, resistance to cytotoxic drugs. Kaufman et al., *Meth. in Enzymology* 185:487–511, 1990, describes several selection schemes, such as dihydrofolate reductase (DHFR) resistance. A suitable host strain for DHFR selection can be CHO strain DX-B11, which is deficient in DHFR (Urlaub et al., *Proc. Natl. Acad. Sci. USA* 77:4216–4220, 1980. A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; and Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, pp. 529–534, 1997; and PCT Application WO 97/25420) and the tripartite leader (TPL) and VA gene RNAs from Adenovirus 2 (Gingeras et al., *J. Biol. Chem.* 257:13475–13491, 1982). The internal ribosome entry site (IRES) sequences of viral origin allows dicistronic mRNAs to be translated efficiently (Oh et al., *Current Opinion in Genetics and Development* 3:295–300, 1993; Ramesh et al., *Nucleic Acids Research* 24:2697–2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150–161, 1997, and p2A5I described by Morris et al., *Animal Cell Technology*, pp. 529–534, 1997.

A useful high expression vector, pCAVNOT, has been described by Mosley et al., *Cell* 59:335–348, 1989. Other expression vectors for use in mammalian host cells can be constructed as disclosed by Okayama et al., *Mol. Cell. Biol.* 3:280, 1983). A useful system for stable high level expression of mammalian cDNAs in C127 murine mammary epithelial cells can be constructed substantially as described by Cosman et al., *Mol. Immunol.* 23:935, 1986. A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, the native signal peptide may be replaced by a heterologous signal peptide or leader sequence, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., *Nature* 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof.

Isolation and Purification

The "isolated" polypeptides or fragments thereof encompassed by this invention are polypeptides or fragments that are not in an environment identical to an environment in which it or they can be found in nature. The "purified" polypeptides or fragments thereof encompassed by this invention are essentially free of association with other proteins or polypeptides, for example, as a purification product of recombinant expression systems such as those described above or as a purified product from a non-recombinant source such as naturally occurring cells and/or tissues.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include the poly-His or other antigenic identification peptides described above as well as the Fc moieties described previously.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, ocetyl, octyldecyl or other aliphatic groups) can be employed to further purify the polypeptides. Some or all of the foregoing purification steps, in various combinations, are well known and can be employed to provide an isolated and purified recombinant protein.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

In this aspect of the invention, polypeptide-binding proteins, such as the anti-polypeptide antibodies of the invention or other proteins that may interact with the polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner.

Alternatively, mixtures of cells suspected of containing polypeptide-expressing cells of the invention first can be incubated with a biotinylated polypeptide-binding protein of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the polypeptide-binding cells to the beads. Use of avidin-coated beads is known in the art. See, Berenson et al., *J. Cell. Biochem.*, 10D:239, 1986. Wash of unbound material and the release of the bound cells is performed using conventional methods.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

Assays

The purified polypeptides of the invention (including proteins, polypeptides, fragments, variants, oligomers, and other forms) may be tested for the ability to bind ss3939 binding partners, such as polysaccharide moieties, in any suitable assay, such as a conventional binding assay. To illustrate, the polypeptide may be labeled with a detectable reagent (e.g., a radionuclide, chromophore, enzyme that catalyzes a colorimetric or fluorometric reaction, and the like). The labeled polypeptide is contacted with cells expressing the binding partner (e.g., polysaccharide moieties). The cells then are washed to remove unbound labeled polypeptide, and the presence of cell-bound label is determined by a suitable technique, chosen according to the nature of the label.

One example of a binding assay procedure is as follows. A recombinant expression vector containing ss3939 cDNA fused to an Fc domain is constructed using methods well known in the art. Soluble ss3939 comprises an N-terminal extracellular domain (preferably amino acids 22 to 227) or an N-terminal extracellular domain and a C-terminal cytoplasmic domain with the transmembrane region removed. CV1-EBNA-1 cells in 10 $cm^2$ dishes are transfected with the recombinant expression vector. CV-1/EBNA-1 cells (ATCC CRL 10478) constitutively express EBV nuclear antigen-1 driven from the CMV immediate-early enhancer/promoter. CV1-EBNA-1 was derived from the African Green Monkey kidney cell line CV-1 (ATCC CCL 70), as described by McMahan et al., *EMBO J.* 10:2821, 1991.

The transfected cells are cultured for 24 hours, and the cells in each dish then are split into a 24-well plate. After culturing an additional 48 hours, medium containing the soluble ss3939/Fc protein is collected from the transfected cells (about $4 \times 10^4$ cells/well), and the amount of ss3939/Fc is quantitated using standard methods in the art.

Cells expressing the binding partner moieties are cultured and washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated for 1 hour at 37° C. with various concentrations of, for example, soluble ss3939/Fc polypeptides. Cells then are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fe portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Autogamma counter. Affinity calculations (Scatchard, *Ann. N.Y. Acad. Sci.* 51:660, 1949) are generated on RS/1 (BBN Software, Boston, Mass.) run on a Microvax computer.

Another type of suitable binding assay is a competitive binding assay. To illustrate, biological activity of a variant may be determined by assaying for the variant's ability to compete with the native protein for binding to the binding partner.

Competitive binding assays can be performed by conventional methodology. Reagents that may be employed in competitive binding assays include radiolabeled soluble ss3939 or radiolabeled intact cells expressing ss3939 (endogenous or recombinant) on the cell surface. For example, a radiolabeled soluble ss3939 fragment can be used to compete with a soluble ss3939 variant for binding to cell surface binding partner. Instead of intact cells, one could substitute a soluble ss3939/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes radiolabeled soluble ss3939, such as a soluble ss3939/Fc fusion protein, and intact cells expressing polysaccharide moieties. Qualitative results can be obtained by competitive autoradiographic plate binding assays, while Scatchard plots (Scatchard, *Ann. N.Y. Acad. Sci.* 51:660, 1949) may be utilized to generate quantitative results.

Use of ss3939 Nucleic Acid or Oligonucleotides

In addition to being used to express polypeptides as described above, the nucleic acids of the invention, including DNA, RNA, mRNA, and oligonucleotides thereof can be used:

- as probes to identify nucleic acids encoding proteins homologous to ss3939;
- to identify human chromosome number 11;
- to map genes on human chromosome number 11;
- to identify genes associated with certain diseases, syndromes, or other conditions associated with human chromosome number 11;
- as single-stranded sense or antisense oligonucleotides, to inhibit expression of polypeptide encoded by the ss3939 gene;
- to help detect defective genes in an individual; and
- for gene therapy.

Probes

Among the uses of nucleic acids of the invention is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence.

Because homologs of SEQ ID NO:1 from other mammalian species are contemplated herein, probes based on the human DNA sequence of SEQ ID NO:1 may be used to screen cDNA libraries derived from other mammalian species, using conventional cross-species hybridization techniques.

Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified.

Chromosome Mapping

All or a portion of the nucleic acids of SEQ ID NO:1, including oligonucleotides, can be used by those skilled in the art using well-known techniques to identify the human chromosome 11, and the specific locus thereof. Useful techniques include, but are not limited to, using the sequence or portions, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

For example, chromosomes can be mapped by radiation hybrid mapping. First, PCR is performed using the Whitehead Institute/MIT Center for Genome Research Genebridge4 panel of 93 radiation hybrids (http://www-genome.wi.mit.edu/ftp/distribution/human_STS_releases/july97/rhmap/genebridge4.html). Primers are used which lie within a putative exon of the gene of interest and which amplify a product from human genomic DNA, but do not amplify hamster genomic DNA. The results of the PCRs are converted into a data vector that is submitted to the Whitehead/MIT Radiation Mapping site on the internet (http://www-seq.wi.mit.edu). The data is scored and the chromosomal assignment and placement relative to known Sequence Tag Site (STS) markers on the radiation hybrid map is provided. The following web site provides additional information about radiation hybrid mapping: http://www-genome.wi.mit.edu/ftp/distribution/human_STS_releases/july97/07-97.INTRO.html).

Identifying Associated Diseases

As set forth below, SEQ ID NO:1 has been mapped by radiation hybrid mapping to the 11q22 region of chromosome 11. That region is associated with specific diseases which include but are not limited to anal canal carcinoma, breast cancer, and lung cancer. Thus, the nucleic acid of SEQ ID NO:1 or a fragment thereof can be used by one skilled in the art using well-known techniques to analyze abnormalities associated with gene mapping to chromosome 11. This enables one to distinguish conditions in which this marker is rearranged or deleted. In addition, nucleotides of SEQ ID NO:1 or a fragment thereof can be used as a positional marker to map other genes of unknown location.

The DNA may be used in developing treatments for any disorder mediated (directly or indirectly) by defective, or insufficient amounts of, the genes corresponding to the nucleic acids of the invention. Disclosure herein of native nucleotide sequences permits the detection of defective genes, and the replacement thereof with normal genes. Defective genes may be detected in in vitro diagnostic assays, and by comparison of a native nucleotide sequence disclosed herein with that of a gene derived from a person suspected of harboring a defect in this gene.

Sense-Antisense

Other useful fragments of the nucleic acids include antisense or sense oligonucleotides comprising a single-stranded nucleic acid sequence (either RNA or DNA) capable of binding to target mRNA (sense) or DNA (antisense) sequences. Antisense or sense oligonucleotides, according to the present invention, comprise a fragment of DNA (SEQ ID NO:1). Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein et al., *Cancer Res.* 48:2659, 1988; and van der Krol et al., *BioTechniques* 6:958, 1988.

Binding of antisense or sense oligonucleotides to target nucleic acid sequences results in the formation of duplexes that block or inhibit protein expression by one of several means, including enhanced degradation of the mRNA by RNAseH, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, lipofection, $CaPO_4$-mediated DNA transfection, electroporation, or by using gene transfer vectors such as Epstein-Barr virus.

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Use of ss3939 Polypeptide and Fragmented Polypeptides
Uses include, but are not limited to, the following:
Purifying proteins and measuring activity thereof
Delivery Agents
Therapeutic and Research Reagents
Molecular weight and Isoelectric focusing markers
Controls for peptide fragmentation
Identification of unknown proteins
Preparation of Antibodies
Purification Reagents Each of the polypeptides of the invention finds use as a protein purification reagent. For example, the polypeptides may be used to purify polysaccharide moieties. In particular embodiments, a polypeptide (in any form described herein that is capable of binding polysaccharide moieties) is attached to a solid support by conventional procedures. As one example, affinity chromatography columns containing functional groups that will react with functional groups on amino acid side chains of proteins are available (Pharmacia Biotech, Inc., Piscataway, N.J.). In an alternative, a polypeptide/Fc protein (as discussed above) is attached to Protein A- or Protein G-containing chromatography columns through interaction with the Fc moiety.

The polypeptide also finds use in purifying or identifying cells that express polysaccharide moieties on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing polysaccharide expressing cells are contacted with the solid phase having the polypeptides thereon. Cells expressing polysaccharide moieties on the cell surface bind to the fixed polypeptides, and unbound cells then are washed away.

Alternatively, the polypeptides can be conjugated to a detectable moiety, then incubated with cells to be tested for polysaccharide expression. After incubation, unbound labeled matter is removed and the presence or absence of the detectable moiety on the cells is determined.

In a further alternative, mixtures of cells suspected of containing polysaccharide moieties are incubated with biotinylated polypeptides. Incubation periods are typically at least one hour in duration to ensure sufficient binding. The resulting mixture then is passed through a column packed with avidin-coated beads, whereby the high affinity of biotin for avidin provides binding of the desired cells to the beads. Procedures for using avidin-coated beads are known (Berenson et al., *J. Cell. Biochem.*, 10D:239, 1986). Washing to remove unbound material, and the release of the bound cells, are performed using conventional methods.

Measuring Activity

Polypeptides also find use in measuring the biological activity of polysaccharide moieties in terms of their binding affinity. The polypeptides thus may be employed by those conducting "quality assurance" studies, e.g., to monitor shelf life and stability of protein under different conditions. For example, the polypeptides may be employed in a binding affinity study to measure the biological activity of polysaccharide moieties that have been stored at different temperatures, or isolated from different cell types. The proteins also may be used to determine whether biological activity is retained after modification of a polysaccharide moiety (e.g., chemical modification, truncation, mutation, etc.). The binding affinity of the modified polysaccharide moiety is compared to that of an unmodified polysaccharide moiety to detect any adverse impact of the modifications on biological activity of polysaccharide moieties The biological activity of a polysaccharide moiety thus can be ascertained before it is used in a research study, for example.

Delivery Agents

The polypeptides also find use as carriers for delivering agents attached thereto to cells bearing ss3939 binding partners such as polysaccharide moieties. The polypeptides thus can be used to deliver diagnostic or therapeutic agents to such cells (or to other cell types found to express ss3939 binding partners on the cell surface) in in vitro or in vivo procedures.

Detectable (diagnostic) and therapeutic agents that may be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}I$, $^{131}I$, $^{99m}Tc$, $^{111}In$, and $^{76}Br$. Examples of radionuclides suitable for therapeutic use are $^{131}I$, $^{211}At$, $^{77}Br$, $^{186}Re$, $^{188}Re$, $^{212}Pb$, $^{212}Bi$, $^{109}Pd$, $^{64}Cu$, and $^{67}Cu$.

Such agents may be attached to the polypeptide by any suitable conventional procedure. The polypeptide comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to polypeptides by using a suitable bifunctional chelating agent, for example.

Conjugates comprising polypeptides and a suitable diagnostic or therapeutic agent (preferably covalently linked) are thus prepared. The conjugates are administered or otherwise employed in an amount appropriate for the particular application.

Therapeutic Agents

Polypeptides of the invention may be used in developing treatments for any disorder mediated (directly or indirectly) by defective, or insufficient amounts of the polypeptides. These polypeptides may be administered to a mammal afflicted with such a disorder.

The polypeptides may also be employed in inhibiting a biological activity of ss3939 binding partners, in in vitro or in vivo procedures. For example, a purified polypeptide may be used to inhibit binding of endogenous ss3939 to cells expressing surface binding partners, for example polysaccharide moieties. Thus, biological effects that result from the binding of endogenous ss3939 to its cognate binding partner are inhibited.

In addition, ss3939 may be administered to a mammal to treat an ss3939-mediated disorder (e.g., a disorder caused by a mutant form of ss3939) or an ss3939 binding partner-mediated disorder. Such ss3939- and ss3939 binding partner-mediated disorders include conditions caused (directly or indirectly) or exacerbated by ss3939 or ss3939 binding partners.

Compositions of the present invention may contain a polypeptide in any form described herein, such as native proteins, variants, derivatives, oligomers, and biologically active fragments. In particular embodiments, the composition comprises a soluble polypeptide or an oligomer comprising soluble ss3939 polypeptides.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences*, 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids in physiologically acceptable formulations are also contemplated. DNA may be formulated for injection, for example.

Research Agents

Another use of the polypeptide of the present invention is as a research tool for studying the biological effects that result from inhibiting ss3939 binding partner/ss3939 interactions on different cell types. Polypeptides also may be employed in in vitro assays for detecting ss3939 binding partners or the interactions thereof.

Another embodiment of the invention relates to uses of ss3939 to study cell signal transduction. ss3939, like other immune cell receptors, could play a central role in immune responses which includes cellular signal transduction, antigen uptake, and antigen presentation. As such, alterations in the expression and/or activation of ss3939 can have profound effects on a plethora of cellular processes. Expression of cloned ss3939, functionally inactive mutants of ss3939, or the cytoplasmic domain can be used to identify the role a particular protein plays in mediating specific signaling events.

Cellular signaling often involves a molecular activation cascade, during which a receptor propagates a ligand-receptor mediated signal by specifically activating intracellular kinases which phosphorylate target substrates. These substrates can themselves be kinases which become activated following phosphorylation. Alternatively, they can be adaptor molecules that facilitate down stream signaling through protein-protein interaction following phosphorylation. Regardless of the nature of the substrate molecule(s), expressed functionally active versions of ss3939, for example the ss3939 cytoplasmic domain, can be used in assays such as the yeast 2-hybrid assay to identify what substrate(s) are recognized and activated by the cytoplasmic domain of ss3939. As such, these novel ss3939 polypeptides can be used as reagents to identify novel molecules involved in signal transduction pathways.

In yet another embodiment, the ss3939 polypeptides of the invention share homology to proteins, such as the macrophage mannose receptor and DEC205, which function as antigen uptake receptors, specifically for bacterial antigens (such as bacterial surface polysaccharides). Since ss3939 was identified in dendritic cells, it should help define and maybe improve the function of dendritic cells.

Molecular Weight, Isoelectric Point Markers

The polypeptides of the present invention can be subjected to fragmentation into smaller peptides by chemical and enzymatic means, and the peptide fragments so produced can be used in the analysis of other proteins or polypeptides. For example, such peptide fragments can be used as peptide molecular weight markers, peptide isoelectric point markers, or in the analysis of the degree of peptide fragmentation. Thus, the invention also includes these polypeptides and peptide fragments, as well as kits to aid in the determination of the apparent molecular weight and isoelectric point of an unknown protein and kits to assess the degree of fragmentation of an unknown protein.

Although all methods of fragmentation are encompassed by the invention, chemical fragmentation is a preferred embodiment, and includes the use of cyanogen bromide to cleave under neutral or acidic conditions such that specific cleavage occurs at methionine residues (E. Gross, *Methods in Enz.* 11:238–255, 1967). This can further include additional steps, such as a carboxymethylation step to convert cysteine residues to an unreactive species.

Enzymatic fragmentation is another preferred embodiment, and includes the use of a protease such as Asparaginylendo-peptidase, Arginylendo-peptidase, *Achromobacter* protease I, Trypsin, *Staphlococcus aureus* V8 protease, Endoproteinase Asp-N, or Endoproteinase Lys-C under conventional conditions to result in cleavage at specific amino acid residues. Asparaginylendo-peptidase can cleave specifically on the carboxyl side of the asparagine residues present within the polypeptides of the invention. Arginylendo-peptidase can cleave specifically on the carboxyl side of the arginine residues present within these polypeptides. *Achromobacter* protease I can cleave specifically on the carboxyl side of the lysine residues present within the polypeptides (Sakiyama and Nakat, U.S. Pat. No. 5,248,599; T. Masaki et al., *Biochim. Biophys. Acta* 660:44–50, 1981; T. Masaki et al., *Biochim. Biophys. Acta* 660:51–55, 1981). Trypsin can cleave specifically on the carboxyl side of the arginine and lysine residues present within polypeptides of the invention. Enzymatic fragmentation may also occur with a protease that cleaves at multiple amino acid residues. For example, *Staphlococcus aureus* V8 protease can cleave specifically on the carboxyl side of the aspartic and glutamic acid residues present within polypeptides (D. W. Cleveland, *J. Biol. Chem.* 3:1102–1106, 1977). Endoproteinase Asp-N can cleave specifically on the amino side of the asparagine residues present within polypeptides. Endoproteinase Lys-C can cleave specifically on the carboxyl side of the lysine residues present within polypeptides of the invention. Other enzymatic and chemical treatments can likewise be used to specifically fragment these polypeptides into a unique set of specific peptides.

Of course, the peptides and fragments of the polypeptides of the invention can also be produced by conventional recombinant processes and synthetic processes well known in the art. With regard to recombinant processes, the polypeptides and peptide fragments encompassed by invention can have variable molecular weights, depending upon the host cell in which they are expressed. Glycosylation of polypeptides and peptide fragments of the invention in various cell types can result in variations of the molecular weight of these pieces, depending upon the extent of modification. The size of these pieces can be most heterogeneous with fragments of polypeptide derived from the extracellular portion of the polypeptide. Consistent polypeptides and peptide fragments can be obtained by using polypeptides derived entirely from the transmembrane and cytoplasmic regions, pretreating with N-glycanase to remove glycosylation, or expressing the polypeptides in bacterial hosts.

The molecular weight of these polypeptides can also be varied by fusing additional peptide sequences to both the amino and carboxyl terminal ends of polypeptides of the invention. Fusions of additional peptide sequences at the amino and carboxyl terminal ends of polypeptides of the invention can be used to enhance expression of these polypeptides or aid in the purification of the protein. In addition, fusions of additional peptide sequences at the amino and carboxyl terminal ends of polypeptides of the invention will alter some, but usually not all, of the fragmented peptides of the polypeptides generated by enzymatic or chemical treatment. Of course, mutations can be introduced into polypeptides of the invention using routine and known techniques of molecular biology. For example, a mutation can be designed so as to eliminate a site of proteolytic cleavage by a specific enzyme or a site of cleavage by a specific chemically induced fragmentation procedure. The elimination of the site will alter the peptide fingerprint of polypeptides of the invention upon fragmentation with the specific enzyme or chemical procedure.

The polypeptides and the resultant fragmented peptides can be analyzed by methods including sedimentation, electrophoresis, chromatography, and mass spectrometry to determine their molecular weights. Because the unique amino acid sequence of each piece specifies a molecular weight, these pieces can thereafter serve as molecular weight markers using such analysis techniques to assist in the determination of the molecular weight of an unknown protein, polypeptides or fragments thereof. The molecular weight markers of the invention serve particularly well as molecular weight markers for the estimation of the apparent molecular weight of proteins that have similar apparent molecular weights and, consequently, allow increased accuracy in the determination of apparent molecular weight of proteins.

When the invention relates to the use of fragmented peptide molecular weight markers, those markers are preferably at least 10 amino acids in size. More preferably, these fragmented peptide molecular weight markers are between 10 and 100 amino acids in size. Even more preferable are fragmented peptide molecular weight markers between 10 and 50 amino acids in size and especially between 10 and 35 amino acids in size. Most preferable are fragmented peptide molecular weight markers between 10 and 20 amino acids in size.

Among the methods for determining molecular weight are sedimentation, gel electrophoresis, chromatography, and mass spectrometry. A particularly preferred embodiment is denaturing polyacrylamide gel electrophoresis (U. K. Laemmli, *Nature* 227:680–685, 1970). Conventionally, the method uses two separate lanes of a gel containing sodium dodecyl sulfate and a concentration of acrylamide between 6–20%. The ability to simultaneously resolve the marker and the sample under identical conditions allows for increased accuracy. It is understood, of course, that many different techniques can be used for the determination of the molecular weight of an unknown protein using polypeptides of the invention, and that this embodiment in no way limits the scope of the invention.

Each unglycosylated polypeptide or fragment thereof has a pI that is intrinsically determined by its unique amino acid sequence (which pI can be estimated by the skilled artisan using any of the computer programs designed to predict pI values currently available, calculated using any well-known amino acid pKa table, or measured empirically). Therefore these polypeptides and fragments thereof can serve as specific markers to assist in the determination of the isoelectric point of an unknown protein, polypeptide, or fragmented peptide using techniques such as isoelectric focusing. These polypeptide or fragmented peptide markers serve particularly well for the estimation of apparent isoelectric points of unknown proteins that have apparent isoelectric points close to that of the polypeptide or fragmented peptide markers of the invention.

The technique of isoelectric focusing can be further combined with other techniques such as gel electrophoresis to simultaneously separate a protein on the basis of molecular weight and charge. The ability to simultaneously resolve these polypeptide or fragmented peptide markers and the unknown protein under identical conditions allows for increased accuracy in the determination of the apparent isoelectric point of the unknown protein. This is of particular interest in techniques, such as two dimensional electrophoresis (T. D. Brock and M. T. Madigan, *Biology of Microorganisms* 76–77 (Prentice Hall, 6th ed. 1991)), where the nature of the procedure dictates that any markers should be resolved simultaneously with the unknown protein. In addition, with such methods, these polypeptides and fragmented peptides thereof can assist in the determination of both the isoelectric point and molecular weight of an unknown protein or fragmented peptide.

Polypeptides and fragmented peptides can be visualized using two different methods that allow a discrimination between the unknown protein and the molecular weight markers. In one embodiment, the polypeptide and fragmented peptide molecular weight markers of the invention can be visualized using antibodies generated against these markers and conventional immunoblotting techniques. This detection is performed under conventional conditions that do not result in the detection of the unknown protein. It is understood that it may not be possible to generate antibodies against all polypeptide fragments of the invention, since small peptides may not contain immunogenic epitopes. It is further understood that not all antibodies will work in this assay; however, those antibodies which are able to bind polypeptides and fragments of the invention can be readily determined using conventional techniques.

The unknown protein is also visualized by using a conventional staining procedure. The molar excess of unknown protein to polypeptide or fragmented peptide molecular weight markers of the invention is such that the conventional staining procedure predominantly detects the unknown protein. The level of these polypeptide or fragmented peptide molecular weight markers is such as to allow little or no detection of these markers by the conventional staining method. The preferred molar excess of unknown protein to polypeptide molecular weight markers of the invention is between 2 and 100,000 fold. More preferably, the preferred molar excess of unknown protein to these polypeptide molecular weight markers is between 10 and 10,000 fold and especially between 100 and 1,000 fold.

It is understood of course that many techniques can be used for the determination and detection of molecular weight and isoelectric point of an unknown protein, polypeptides, and fragmented peptides thereof using these polypeptide molecular weight markers and peptide fragments thereof and that these embodiments in no way limit the scope of the invention.

In another embodiment, the analysis of the progressive fragmentation of the polypeptides of the invention into specific peptides (D. W. Cleveland et al., *J. Biol. Chem.* 252:1102–1106, 1977), such as by altering the time or temperature of the fragmentation reaction, can be used as a control for the extent of cleavage of an unknown protein. For example, cleavage of the same amount of polypeptide and unknown protein under identical conditions can allow for a direct comparison of the extent of fragmentation. Conditions that result in the complete fragmentation of the polypeptide can also result in complete fragmentation of the unknown protein.

As to the specific use of the polypeptides and fragmented peptides of the invention as molecular weight markers, the fragmentation of the purified polypeptide or a fragment thereof with cyanogen bromide generates a unique set of fragmented peptide molecular weight markers. Cyanogen bromide cleavage of the purified extracellular domain of ss3939 would generate fragments with molecular weights of approximately 1.33, 1.55, 6.48, and 14.2 Kilodaltons (kDa) in the absence of glycosylation. The distribution of methionine residues determines the number of amino acids in each peptide and the unique amino acid composition of each peptide determines its molecular weight.

In addition, the preferred purified extracellular domain of ss3939 is 23.56 kDa in the absence of glycosylation (although the polypeptide of the invention (SEQ ID NO:2) has a calculated molecular weight of approximately 40.1 kDa in the absence of glycosylation).

Where an intact protein is used, the use of the preferred polypeptide molecular weight markers allows increased accuracy in the determination of apparent molecular weight of proteins that have apparent molecular weights close to 40.1 kDa.

Finally, as to the kits that are encompassed by the invention, the constituents of such kits can be varied, but typically contain the polypeptide and fragmented peptide molecular weight markers. Also, such kits can contain the polypeptides wherein a site necessary for fragmentation has been removed. Furthermore, the kits can contain reagents for the specific cleavage of the polypeptide and the unknown protein by chemical or enzymatic cleavage. Kits can further contain antibodies directed against polypeptides or fragments thereof of the invention.

Identification of Unknown Proteins

As set forth above, a polypeptide or peptide fingerprint can be entered into or compared to a database of known proteins to assist in the identification of the unknown protein using mass spectrometry (W. J. Henzel et al., *Proc. Natl. Acad. Sci. USA* 90:5011–5015, 1993; D. Fenyo et al., *Electrophoresis* 19:998–1005, 1998). A variety of computer software programs to facilitate these comparisons are accessible via the Internet, such as Protein Prospector (Internet site: prospector.uscf.edu), MultiIdent (Internet site: www.expasy.ch/sprot/multiident.html), PeptideSearch (Internet site: www.mann.embl-heiedelberg.de...deSearch/FR_PeptideSearch Form.html), and ProFound (Internet site: www.chait-sgi.rockefeller.edu/cgi-bin/prot-id-frag.html). These programs allow the user to specify the cleavage agent and the molecular weights of the fragmented peptides within a designated tolerance. The programs compare these molecular weights to protein databases to assist in determining the identity of the unknown protein.

In addition, a polypeptide or peptide digest can be sequenced using tandem mass spectrometry (MS/MS) and the resulting sequence searched against databases (J. K. Eng et al., *J. Am. Soc. Mass Spec.* 5:976–989, 1994; M. Mann et al., *Anal. Chem.* 66:43904399, 1994; J. A. Taylor et al., *Rapid Comm. Mass Spec.* 11:1067–1075, 1997). Searching programs that can be used in this process exist on the Internet, such as Lutefisk 97 (Internet site: www.lsbc.com:70/Lutefisk97.html), and the Protein Prospector, Peptide Search and ProFound programs described above. Therefore, adding the sequence of a gene and its predicted protein sequence and peptide fragments to a sequence database can aid in the identification of unknown proteins using tandem mass spectrometry.

Antibodies

Antibodies that are immunoreactive with the polypeptides of the invention are provided herein. Such antibodies specifically bind to the polypeptides via the antigen-binding sites of the antibody (as opposed to non-specific binding). Thus, the polypeptides, fragments, variants, fusion proteins, etc., as set forth above may be employed as "immunogens"

in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology*. 3:9, Garland Publishing Inc., 2nd ed., 1996). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology*, 2:14, Garland Publishing Inc., 2nd ed. 1996). Epitopes may be identified by any of the methods known in the art.

Thus, one aspect of the present invention relates to the antigenic epitopes of the polypeptides of the invention. Such epitopes are useful for raising antibodies, in particular monoclonal antibodies, as described in more detail below. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the invention, whether the epitopes have been isolated or remain part of the polypeptides, both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York, 1980; and *Antibodies: A Laboratory Manual*, Harlow and Land (eds.), Cold Spring Harbor Laboratory Press, Cold Spring Harbor, N.Y., 1988.

Hybridoma cell lines that produce monoclonal antibodies specific for the polypeptides of the invention are also contemplated herein. Such hybridomas may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al., *Nature* 332:323, 1988; Liu et al., *PNAS* 84:3439, 1987; Larrick et al., *Bio/Technology* 7:934, 1989; and Winter et al., *TIPS* 14:139, 1993. Procedures to generate antibodies transgenically can be found in GB 2,272,440, U.S. Pat. Nos. 5,569,825 and 5,545,806 and related patents claiming priority therefrom, all of which are incorporated by reference herein.

Antigen-binding fragments of the antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

In one embodiment, the antibodies are specific for the polypeptides of the present invention and do not cross-react with other proteins. Screening procedures by which such antibodies may be identified are well known, and may involve immunoaffinity chromatography, for example.

Uses Thereof

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that additionally can block binding of the polypeptides of the invention to the binding partner may be used to inhibit a biological activity that results from such binding. Such blocking antibodies may be identified using any suitable assay procedure, such as by testing antibodies for the ability to inhibit binding of ss3939 to certain cells expressing the binding partner. Alternatively, blocking antibodies may be identified in assays for the ability to inhibit a biological effect that results from binding of ss3939 to target cells. Antibodies may be assayed for the ability to inhibit ss3939-mediated cell lysis, for example.

In addition, in view of ss3939's characterization as a type 1 membrane protein, it may be a receptor for either a soluble or membrane-bound human protein. Thus, antibodies to ss3939 may either inhibit ss3939/binding partner interactions or perhaps mimic ligands that bind to ss3939. Thus, antibodies against ss3939 can be used to inhibit or to mimic the ligand binding effects.

The antibodies of the invention may be administered in vivo to treat disorders caused or exacerbated (directly or indirectly) by the interaction of ss3939 with the cell surface binding partner. A therapeutic method involves in vivo administration of a blocking antibody to a mammal in an amount effective in inhibiting an ss3939-mediated biological activity. Monoclonal antibodies are generally preferred for use in such therapeutic methods. In one embodiment, an antigen-binding antibody fragment is employed.

Antibodies may be screened for agonistic (i.e., ligand-mimicking) properties. Such antibodies, upon binding to cell surface polysaccharide moieties, induce biological effects (e.g., transduction of biological signals) similar to the biological effects induced when ss3939 binds to cell surface polysaccharide moieties.

Compositions comprising an antibody that is directed against ss3939, and a physiologically acceptable diluent, excipient, or carrier, are provided herein. Suitable components of such compositions are as described above for compositions containing ss3939 proteins.

Also provided herein are conjugates comprising a detectable (e.g., diagnostic) or therapeutic agent, attached to the antibody. Examples of such agents are presented above. The conjugates find use in in vitro or in vivo procedures.

The following examples are provided to further illustrate particular embodiments of the invention, and are not to be construed as limiting the scope of the present invention.

EXAMPLE 1

Isolation of the Nucleic Acid

The ss3939 cDNA was identified by high-throughput sequencing of human CD34+ bone marrow-derived dendritic cell cDNA libraries.

EXAMPLE 2

Preparation of ss3939/Fc Fusion Protein

A fusion protein was prepared comprising the extracellular domain of ss3939 (amino acids 22–227 of SEQ ID NO:2) and a C-terminal Fc domain, as discussed above. An expression construct was prepared essentially as described in Baum et al., EMBO J., 13:39924001, 1994. First, a DNA fragment encoding the ss3939 signal sequence and extracellular domain was prepared by PCR amplification, digested with the appropriate restriction endonucleases and purified by agarose gel electrophoresis. The DNA fragment was ligated to the Fc coding region of human IgG1 and inserted into expression vector pDC409, and the construct was verified by double-strand DNA sequencing. The expression vector designated pDC409 is a mammalian expression vector derived from the pDC406 vector described in McMahan et al., EMBO J., 10:2821–2832, 1991; hereby incorporated by reference. Features added to pDC409 (compared to pDC406) include additional unique restriction sites in the multiple cloning site (mcs); three stop codons (one in each reading frame) positioned downstream of the mcs; and a T7 polymerase promoter, downstream of the mcs, which facilitates sequencing of DNA inserted into the mcs. Alternatively, a C-terminal leucine zipper peptide can be fused to the ss3939 extracellular domain in the same fashion described above for a C-terminal Fc fusion.

The ss3939/Fc expression vector was used to transfect CV1/EBNA cells, and the transfected cells were seeded into tissue culture roller bottles. The transfected cells were grown in tissue culture medium at 37° C. for 34 weeks. The medium was collected and replaced weekly, and the collected and pooled media containing the secreted ss3939/Fc fusion protein was passed through a protein A sepharose column to purify the ss3939/Fc fusion protein. The purified fusion protein was quantified, verified by N-terminal amino acid sequencing, and used for biological evaluation. The ss3939/Fc fusion protein was also used as an immunogen to prepare monoclonal anti-ss3939 antibodies.

EXAMPLE 3

Monoclonal Antibodies

This example illustrates a method for preparing monoclonal antibodies that bind ss3939. Suitable immunogens that may be employed in generating such antibodies include, but are not limited to, purified ss3939 polypeptide or an immunogenic fragment thereof such as the extracellular domain, or fusion proteins containing ss3939 (e.g., a soluble ss3939/Fc fusion protein).

Purified ss3939 can be used to generate monoclonal antibodies immunoreactive therewith, using conventional techniques such as those described in U.S. Pat. No. 4,411,993. Briefly, mice are immunized with ss3939 immunogen emulsified in appropriate adjuvant, such as complete Freund's adjuvant or Titermax adjuvant (Cytrx Corp., Norcross, Ga.), and injected in amounts ranging from 10–100 μg subcutaneously or intraperitoneally. Ten to twelve days later, the immunized animals are boosted with additional ss3939 emulsified in incomplete Freund's adjuvant. Mice are periodically boosted thereafter on a weekly to bi-weekly immunization schedule. Serum samples are periodically taken by retro-orbital bleeding or tail-tip excision to test for ss3939 antibodies by dot blot assay, ELISA (Enzyme-Linked Immunosorbent Assay) or inhibition of ss3939/polysaccharide binding.

Following detection of an appropriate antibody titer, positive animals are provided one last intravenous injection of ss3939 in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified ss3939 by adaptations of the techniques disclosed in Engvall et al., (Immunochem. 8:871, 1971) and in U.S. Pat. No. 4,703,004. A preferred screening technique is the antibody capture technique described in Beckmann et al., (J. Immunol. 144:4212, 1990). Positive hybridoma cells can be injected intraperitoneally into syngeneic BALB/c mice to produce ascites containing high concentrations of anti-ss3939 monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to ss3939.

In a specific embodiment, mice were immunized with the ss3939/Fc fusion protein described in Example 2 emulsified in Titermax adjuvant (Cytrx Corp., Norcross, Ga.) and injected in amounts ranging from 5–25 μg subcutaneously. Two to four weeks later, the immunized animals were boosted with additional ss3939/Fc immunogen emulsified in incomplete Freund's adjuvant. Mice were periodically boosted thereafter on week 5 and again at week 8. Serum samples were periodically taken by retro-orbital bleeding or tail-tip excision to test for ss3939 antibodies by ELISA (Enzyme-Linked Immunosorbent Assay).

Following detection of an appropriate antibody titer, positive animals were provided one last intravenous injection of ss3939/Fc in saline. Three days later, the animals were sacrificed, spleen cells harvested, and spleen cells were fused to a murine myeloma cell line NS1 via a polyethylene glycol-mediated fusion. Hybridoma cells generated from the fusion were plated in multiple microtiter plates in a HAT (hypoxanthine, aminopterin and thymidine) selective medium to inhibit proliferation of non-fused cells, myeloma hybrids, and spleen cell hybrids.

The hybridoma cells were screened for reactivity against recombinant ss3939 polypeptide expressed on the surface of transiently transfected mammalian cells by means of a dried cell ELISA. In this assay the transfected cells were plated in a small volume in a 96-well ELISA microtiter plate and allowed to air dry thus adhering to the plate where they serve as the platecoat antigen in an otherwise standard ELISA assay.

Positive hybridoma cells were injected intraperitoneally into syngeneic BALB/c mice to produce ascites containing high concentrations of anti-ss3939 monoclonal antibodies. Monoclonal antibodies produced in mouse ascites were purified by Protein A affinity chromatography. In this manner, five ss3939-specific monoclonal antibodies were derived.

EXAMPLE 4

Northern Blot Analysis

The tissue distribution of ss3939 is investigated by Northern blot analysis, as follows. An aliquot of a radiolabeled ss3939 coding region probe is added to human multiple tissue Northern blots (Clontech, Palo Alto, Calif.; Biochain; Palo Alto, Calif.) and to Northern blots containing assorted human cell and cell line mRNAs. Hybridization is performed in a solution containing 50% formamide, 5×SSC (0.75M NaCl, 0.075M sodium citrate), 2× Denhardt's, 50 mM potassium phosphate pH 6.5, 1% SDS, 200 µg/mL salmon sperm DNA, and 20 mM N-lauroyl sarcosine at 63° C. overnight, as previously described (March et al., *Nature* 315:641–647, 1985). The blots are then washed in 0.5×SSC, 0.1% SDS at 68° C. for 30 minutes. The cells and tissues with the highest levels of ss3939 mRNA are determined by comparison to control probing with a β-actin-specific or GAPDH-specific probe.

Using this approach, it was determined that ss3939 mRNA is predominantly expressed in cells and cell lines of epithelial origin, including WI-26 VA4 (ATCC CCL 95.1), A172 (ATCC CRL 1620), human foreskin fibroblasts, african green monkey kidney epithelial lines COS-1 (ATCC CRL 1650) and CV-1 (ATCC CCL 70), and human epithelial-like bladder carcinoma T24 (ATCC HTB4).

EXAMPLE 5

Binding Assay ss3939 polypeptides or fragments thereof can be expressed and tested for the ability to bind ss3939 binding partners. The binding assay can be conducted as follows.

An Fc fusion protein, such as ss3939/Fc described in Example 2, comprising the N-terminus of a soluble ss3939 polypeptide fused to an Fc C-terminal domain is employed in the assay. ss3939/Fc is used to test the ability of ss3939 to bind to host cells expressing cognate binding partner, such as polysaccharide moieties, as discussed above. Cells are incubated with ss3939/Fc (1–5 µg/ml) in phosphate buffered saline containing 10% FBS, 10% goat serum, and 10% rabbit serum at 4° C. for about 1 hour. Following incubation, the cells are washed to remove unbound ss3939/Fc and incubated with a biotinylated, goat anti-human IgG$_1$ monoclonal antibody (1–5 µg/ml), and phycoerythrin-conjugated streptavidin (typically diluted 1:100–400), before analysis by fluorescence-activated cell sorting (FACS). The cytometric analysis is conducted on a FACscan (Beckton Dickinson, San Jose, Calif.).

The cells expressing binding partner will show significantly enhanced binding of ss3939/Fc, compared to control cells not expressing binding partner. Using the above method, human umbilical vein endothelial cells were shown to consistently express a surface molecule that binds to ss3939/Fc.

All references cited herein are hereby incorporated by reference in their entirety.

What is claimed is:

1. A method for screening for inhibitors of binding between an ss3939 polypeptide and a binding partner of said ss3939 polypeptide, the method comprising:

a) providing an isolated soluble ss3939 polypeptide comprising the amino acid sequence selected from the group consisting of amino acids 22 through 227 of SEQ ID NO:2, amino acids 24 through 227 of SEQ ID NO:2, and amino acids 25 through 227 of SEQ ID NO:2;

b) bringing said isolated soluble ss3939 polypeptide into contact with human umbilical vein endothelial cells in the presence of and in the absence of a test compound, wherein the binding partner of said ss3939 polypeptide is expressed by human umbilical vein endothelial cells, and wherein said isolated soluble ss3939 polypeptide binds to human umbilical vein endothelial cells; and c) determining if the binding of ss3939 to the human umbilical vein endothelial cells is inhibited by the test compound.

2. The method of claim 1 wherein the binding partner of the ss3939 polypeptide comprises one or more polysaccharide moieties.

3. The method of claim 1 wherein the soluble polypeptide comprises the amino acid sequence of amino acids 22 through 227 of SEQ ID NO: 2.

4. The method of claim 1 wherein the soluble polypeptide is an oligomer.

5. The method of claim 4 wherein the soluble polypeptide is a dimer.

6. The method of claim 1 wherein the soluble polypeptide comprises an Fc polypeptide.

7. The method of claim 1 wherein the soluble polypeptide comprises a leucine zipper.

8. The method of claim 1 wherein the method comprises providing the polypeptide in vitro.

* * * * *